United States Patent [19]

Posso et al.

[11] Patent Number: 5,627,531
[45] Date of Patent: May 6, 1997

[54] MULTI-FUNCTION MENU SELECTION DEVICE

[75] Inventors: Oliver A. Posso, Golden; Julie A. Reichert, Aurora, both of Colo.

[73] Assignee: Ohmeda Inc., Liberty Corner, N.J.

[21] Appl. No.: 315,750

[22] Filed: Sep. 30, 1994

[51] Int. Cl.[6] .................................................. H03M 11/00
[52] U.S. Cl. .................................. 341/22; 341/20; 341/35; 345/184; 345/902
[58] Field of Search .................................. 341/22, 20, 35; 345/146, 157, 160, 173, 184, 156, 902; 200/5 R, 11 R, 14; 128/633, 637, 665

[56] References Cited

U.S. PATENT DOCUMENTS 3,824,354  7/1974  Anderson et al. ..................... 341/20
4,246,452  1/1981  Chandler ................................ 341/20
4,247,845  1/1981  Schmidt et al. ...................... 345/156
5,448,240  9/1995  Morito .................................. 341/35

Primary Examiner—Jeffery Hofsass
Assistant Examiner—Andrew Hill
Attorney, Agent, or Firm—Roger M. Rathbun; Larry R. Cassett; James M. Graziano

[57] ABSTRACT

The menu selection device uses a combination of the rotary position of a rotary optical encoder and the operation of a coaxially mounted push-button switch to enable the user to progress through various layers of a hierarchical menu system. The rotary position of the shaft translates to a menu category which is selected by the user activating the push-button switch. The selection of the menu category allows the user to then sequence through the plurality of menu entries within this menu category by again rotating the shaft. The user selects one of these menu entries by again activating the push-button switch.

36 Claims, 6 Drawing Sheets

MULTI-FUNCTION MENU SELECTION DEVICE

FIELD OF THE INVENTION

This invention relates to electronic instruments and, in particular, to a menu selection device that enables the user to sequence through a hierarchical menu that contains a plurality of menu choices and enter a menu selection by means of a single simple input device.

PROBLEM

It is a problem in the field of electronic instruments to provide a user interface that is both simple to use and performs a data input function in a cost-effective, reliable manner. For portable instruments, an additional consideration is energy efficiency since these devices are battery-powered and can ill afford to have a user interface that consumes a significant amount of power. In the field of medical monitoring apparatus, it is desirable for the instrument to be hand-held, to provide a display that can produce a graphical representation of the parameter that is being measured as well as to have a simple and full-functional user interface that enables the user to set a number of operational characteristics of the instrument. A hand-held instrument has a very limited surface area that can be used for a user interface, yet in many applications, the user must be able to select a plurality of functions and input various information in order to perform the desired function.

The typical user interface includes rotary mechanical switches that make use of mechanical detentes to enable the user to select one of a plurality of predetermined positions, each position corresponding to a function selection. Electrical switch contacts are affixed to the shaft of the rotary switch to translate the mechanical position of the switch to an electrical signal indicative of the user's selection. These rotary switches are highly susceptible to contact contamination, are electrically noisy, and quickly wear. Furthermore, the size of the rotary switch is a function of the number of selections that are provided to the user and can therefore consume a significant amount of space in the hand held instrument. Keyboard type of data entry devices are space intensive, complex, expensive, lack tactile feedback, and do not have a fast response to a user input to change settings.

Therefore, it is a problem in the field of portable monitoring instruments to provide a user interface that enables the user to select functions and/or enter data in a manner that is simple, reliable, and which does not consume a significant amount of power or occupy a significant amount of the instrument surface area.

SOLUTION

The above-described problems are solved and a technical advance achieved in the field by the menu selection device of the present invention which uses the combination of a rotary optical encoder and a switch to perform the user interface function. The rotary optical encoder is coaxially mounted on a shaft with a knob that enables the user to rotate the shaft in either direction. Mechanical detentes are provided to provide tactile feedback to the user and to enable the shaft to be precisely positioned in any one of a number of predetermined rotary positions. The rotary optical encoder operates in a pulsed sampling mode wherein the light-emitting devices contained therein are only activated for a short duration on a frequent basis to sense the position of the shaft yet not consume a significant amount of power. The rotary position of the shaft translates to various menu selections which are displayed to the user by means of a display device.

Additional functionality is provided by a shaft-mounted push-button switch which enables the apparatus to implement a hierarchical menu selection process that combines the rotary position of the shaft and the operation of the push button switch to enable the user to progress through various layers of the hierarchical menu system. The rotary position of the shaft translates to a menu category which is then selected by the user activating the push-button switch. The selection of the menu category allows the user to then sequence through the plurality of menu entries within this menu category by again rotating the shaft. The user selects one of these menu entries by activating the push-button switch. This apparatus is a fairly sophisticated user interface that is compact, energy-efficient, reliable, and can implement a hierarchical menu system.

DETAILED DESCRIPTION

Figure 1:
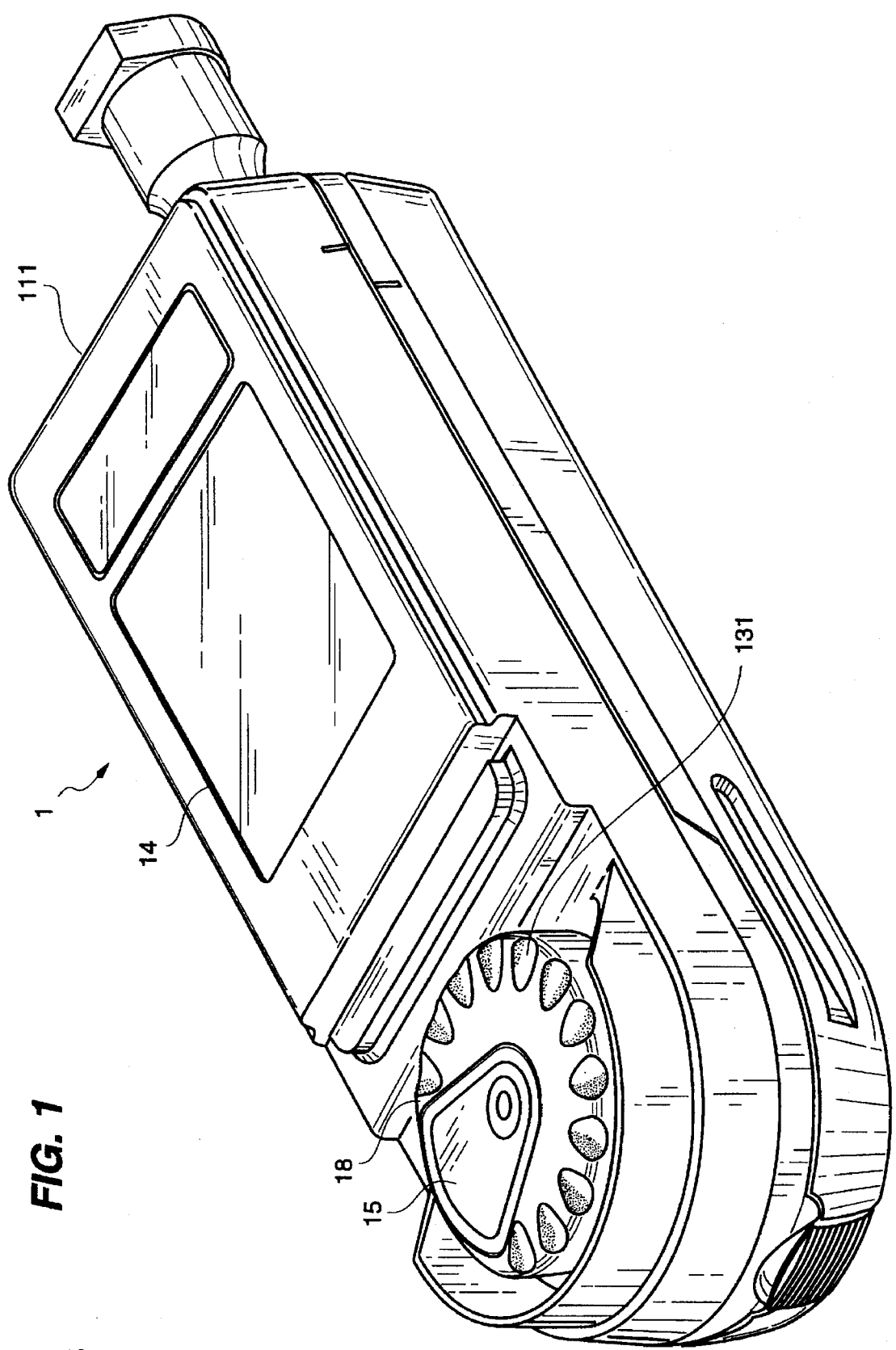
FIG. 1 illustrates in perspective view the menu selection device of the present invention installed in a hand-held instrument.
Figure 2:
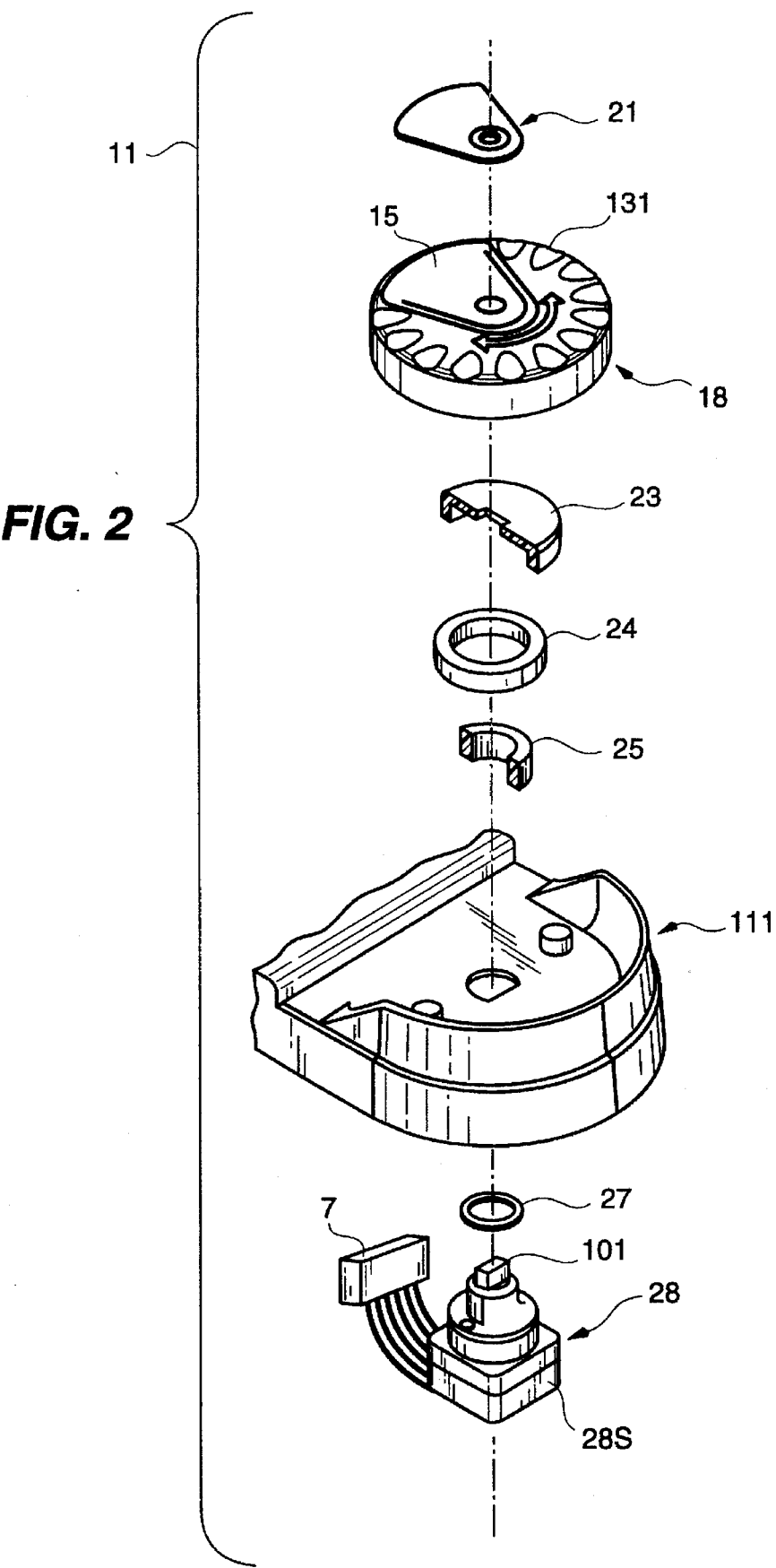
FIG. 2 illustrates an exploded view of the menu selection device of the present invention.

FIG. 1 illustrates a perspective view of a monitoring instrument 1 that makes use of the menu selection device 11 of the present invention and FIG. 2 illustrates an exploded view of the menu selection device 11. The monitoring instrument 1 can be implemented in any of numerous forms and for the purpose of illustration is shown as a hand-held pulse oximeter instrument. This pulse oximeter instrument 1 consists of a substantially rectangular housing of dimensions and contours that allow the instrument 1 to be comfortably held in the user's hand. The pulse oximeter instrument 1 includes a display 10 that is used to provide data to the user, a probe (not shown) that is plugably affixed to the pulse oximeter instrument 1 and that is connectable to a patient to perform measurements of predetermined physiological characteristics of the patient. The menu selection device 11 of the present invention is incorporated in the pulse oximeter instrument 1 and enables the user to select the operating mode of the pulse oximeter instrument 1, as well as to input data into the pulse oximeter instrument 1 as required.

Pulse Oximeter Instrument

The pulse oximeter instrument 1 measures the oxygen saturation of the arterial blood of a patient. The pulse oximeter instrument 1 operates by illuminating the arteriolar bed of a perfused appendage of the patient with light of at least two predetermined wavelengths. The light wavelengths are selected to be highly absorbed by oxygenated and deoxygenated hemoglobin contained in the arterial blood. The pulse oximeter instrument measures the magnitude of the light that passes through the illuminated appendage. The pulsatile component of the light output from the appendage is used to determine the oxygen saturation of the arterial blood flow. Thus, a probe containing a plurality of light sources and a light detector is attached to an appendage of the patient that is rich in arterial blood flow, such as a finger, nasal septum, earlobe, etc., so that the light absorption of the arterial blood and thereby the oxygen saturation thereof, can be directly measured. The output signal produced by the light detector is processed in well known fashion by the measurement apparatus of the pulse oximeter instrument 1 and a resultant numeric value indicative of the oxygen saturation of the arterial blood is produced. It is this value of the oxygen saturation that is displayed to the user.

Menu Selection Device - Architecture

The hand-held pulse oximeter instrument 1 is typically used by the nursing staff to perform measurements on a plurality of patients as the nurse makes patient rounds on a regularly scheduled basis. It is therefore desirable to store the measurements that are performed and to also provide a capability to print out or download the results of the measurements so that a hard copy or a data file version of the measurements can be stored in the patient's permanent record. There is therefore a need to provide a significant amount of functionality in the pulse oximeter instrument 1 and to enable the user to input data of varying types and quantity, as well as to select a subset of features that are to be used in performing the desired measurements. A typical set of menu categories and the individual menu entry selections available under each of these menu categories is illustrated in chart form in FIG. 3. This particular embodiment represents just one of the many possible configurations and is used herein for the purpose of illustrating the capability of the menu selection device 11 of the present invention.

The menu selection device 11 consists of a mechanical mechanism that is operable by the user and an associated set of transducer elements 28 that translate the movement of the mechanical apparatus into electrical signals that can be used by the control circuitry in the pulse oximeter instrument 1 to perform the desired function. The mechanical mechanism that is used herein consists of a shaft 101 that is rotatable about an axis, wherein the shaft 101 projects through the outer housing 111 of the pulse oximeter instrument 1 while the transducer elements 28 are mounted at one end of the shaft 101 and enclosed in the housing 111 to protect them from damage caused by both user handling of the pulse oximeter instrument 1 and the ambient environment. The other end of the shaft 101 typically projects through the outer housing 111 of the pulse oximeter instrument 1 and has attached thereto a selector knob 18 which is the instrumentality that the user manipulates to perform the data input task.

In the preferred embodiment illustrated herein, the selector knob 18 consists of a cylindrical element formed of a suitable material, such as thermoplastic. The selector knob 18 has formed in its top surface thereof a plurality of depressions 131, in the form of smooth scalloped recesses formed therein to provide non-slip rotational control. Each depression 131 corresponds to a mechanical detente that is built into the shaft mechanism so that the user can rotate the selector knob 18 and receive tactile feedback indicative of the selector knob 18 reaching a predefined selector position. The depressions 131 formed in the top surface of the selector knob 18 provide visual feedback to the user that corresponds spatially with the tactile feedback produced by the detentes. The depressions 131 that are formed in the selector knob 18 can correspond to fixed predefined functions, such that the selector knob 18 functions as a traditional selector switch. In this configuration, each selector position corresponds to a defined function which is activated when the user rotates the selector knob 18 to align the depression 131 labeled with that function opposite a selector indicator 132 imprinted on the housing 111. Alternatively, the detente positions and the corresponding depressions 131 in the top surface of the selector knob 18 can be dynamically assigned, such that when the user first activates the pulse oximeter instrument 1, the present position of the selector knob 18 represents the preferred main menu category and other menu category selections initiated by the rotation of the selector knob 18 are designated in terms relative to the initial base position of the selector knob 18. The labelling of the various knob positions is performed dynamically and displayed to the user on a visual readout display device 14.

The selector knob 18 also allows the user to move between various levels in the menu hierarchy and to rapidly change values/settings within a menu category. The selector knob 18 is capable of rotation through 360 degrees, both clockwise and counterclockwise. The full circle of rotation is divided into 16 detented positions. The selector knob 18 is capable of two control functions: rotation and select. The controls that activate these functions are independent of each other and this architecture prevents inadvertent selection of a menu category or menu entry during rotation of the selector knob 18. The select feature allows the user to choose a menu category for operation or to change a setting on the pulse oximeter instrument 1. The select element 15 is recessed below the top control surface of the selector knob 18 to provide both protection from inadvertent actuation and to provide a visual cue to the user of the independent nature of this control. The alphanumeric display 14 provides an indication of the menu categories/entries and oxygen saturation readings. The alphanumeric display 14 displays which menu category is presently active and the user is only able to modify the settings of the pulse oximeter instrument 1 once the user has selected to be in the menu category. In operation, the user views the visual information provided on the readout display device 14 and elects what action to take based on the information that is presented on the display device 14.

In the context of this description, the term "select" refers to the subsection of the top control surface of the selector knob 18 that, when depressed, activates a momentary switch 28S that is mounted behind the shaft 101 of the rotary encoder. The term "at", as used herein, refers to the user being at a menu category but not within it, while the term "in" refers to the user being within a menu category, past the first level structure. Being in a menu category after a select places the user in the position of changing a setting or incrementally selecting lower menu levels. If the menu category is left idle for a predetermined period of time, the control automatically returns to the main menu.

Menu Categories

Figure 3:
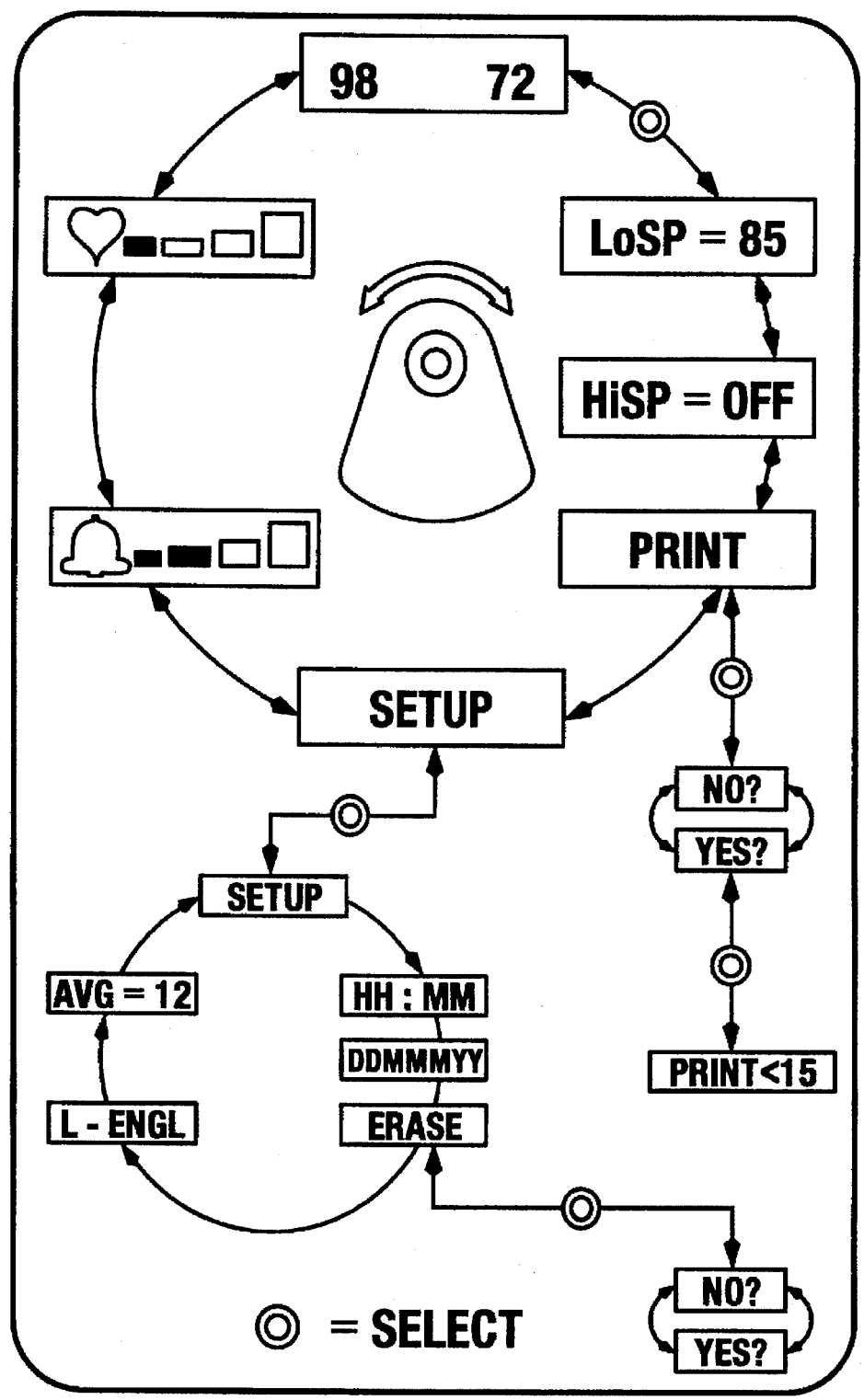
FIG. 3 illustrates the architecture of a typical menu in the menu selection device of the present invention.

The plurality of menu categories are illustrated in the chart of FIG. 3. The default setting menu category is the display of the values of the measured variables. This category is shown on the top of FIG. 3 and the display indicates the measured oxygen saturation of the patient's arterial blood (98) and the patient's pulse rate (72). Clockwise from this baseline position, the first menu category is the "LoSp" category which enables the user to set the alarm limit for a low oxygen saturation reading (presently set a 85). The next menu category in the clockwise direction is the "HiSp" category which enables the user to set the alarm limit for a high oxygen saturation reading (presently set at OFF). The next menu category in the clockwise direction is the "Print" category which enables the user to activate the data download function to print or download the data stored in the pulse oximeter instrument. The next menu category in the clockwise direction is the "Setup" category which enables the user to initialize a number of settings in the pulse oximeter instrument. The next menu category in the clockwise direction is the audible alarm category which enables the user to set the audible level of the alarm for an oxygen saturation reading that exceeds the high or low threshold values that are set by the user. The next menu category in the clockwise direction is the audible pulse category which enables the user to set the audible level of the pulse rate monitor.

Menu Category - Set Low/High Oxygen Saturation Limits

As noted above, there are menu categories for setting the low and high thresholds for the alarm to indicate when the present oxygen saturation measurement is outside of the allowable range of values. These threshold values are set by the user rotating the selector knob 18 to the desired menu category, such as "LoSp", and when the "LoSp" designation appears on the display, activating the select element 15 of the selector knob 18. To select a value for the low oxygen saturation alarm limit, the user turns the selector knob 18 clockwise to raise the limit, counterclockwise to lower the limit. Once the desired low oxygen saturation value alarm limit is displayed on the display, the user presses the select element 15 of the selector knob 18 to set new limit. The operation to set the high oxygen saturation alarm limit is the same as described for the low alarm limit.

Menu Category - Print

The menu category for print activation requires that the user connect the hand held pulse oximeter instrument 1 to a printer device or to a data communication link to download the data that is stored in the memory of the pulse oximeter instrument 1. The pulse oximeter instrument retrieves the identified data and transmits it to the data output device that is connected to the pulse oximeter instrument 1, whether a printer or a data storage element.

Figure 6A:
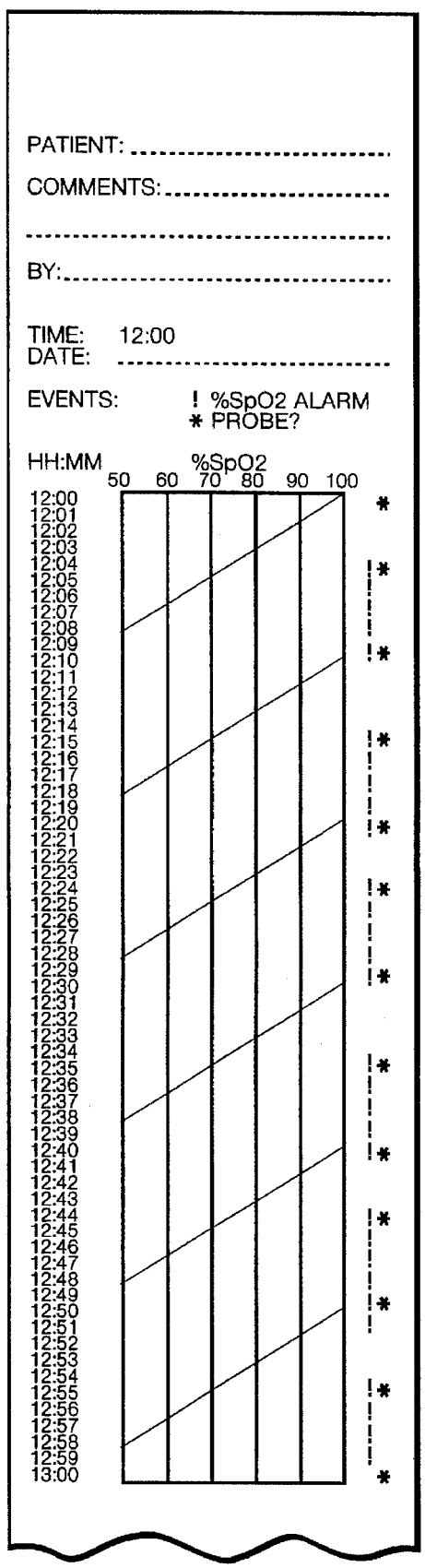
FIGS. 6A and 6B illustrate a typical printout from a pulse oximeter instrument that uses the menu selection device.
Figure 6B:
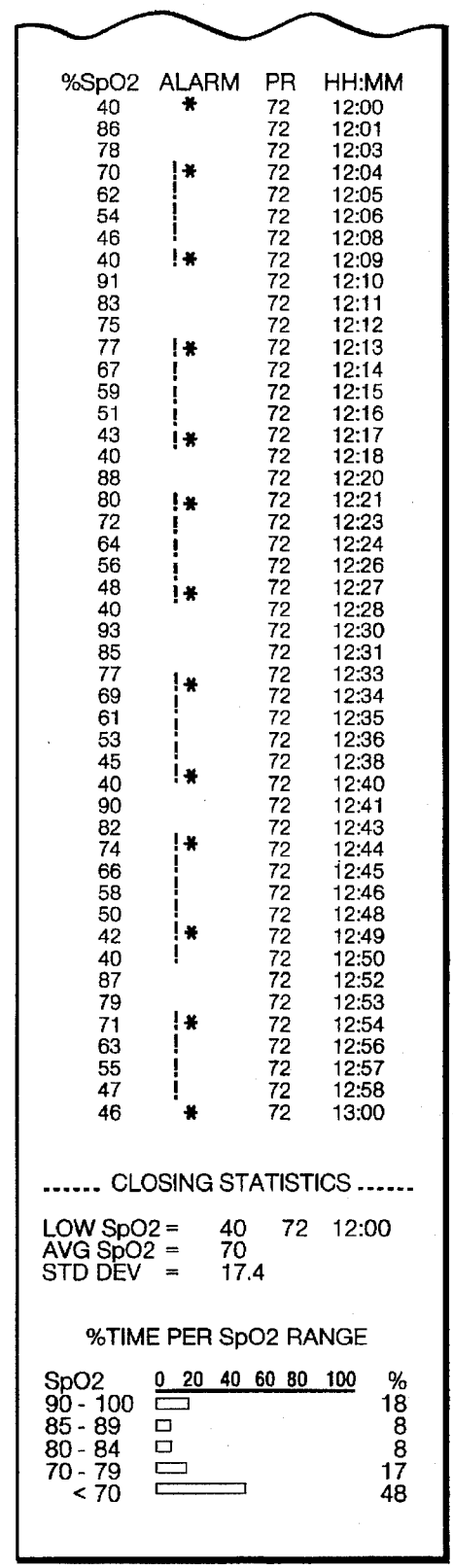

FIGS. 6A and 6B illustrate a typical printout that is output by the pulse oximeter instrument 1. The printout includes all the relevant information that the user sets into the pulse oximeter instrument 1 using the menu selection device 11. The patient identification, alarm limits, date and time of the printout are all printed as header information. The pulse oximeter instrument 1 then prints a chart that indicates the time that the readings were taken, a graph of the oxygen saturation values as well as a listing of the corresponding pulse rate. A summary bar chart is also included to provide the user with a statistical analysis of the specifically displayed readings.

Menu Category - Setup

The "Setup" menu category includes a number of submenu categories. These include the time and date, which are set by the user activating the select element of the selector knob 18 when the time/date submenu category is displayed on the display 14 and then rotating the selector knob 18 to raise or lower the time/date that is presently displayed. Once the desired time/date is present on the display 14, the user can again activate the select element 15 of the selector knob 18 to set the time/date. Another submenu category is the "Erase" function, which operates in a manner analogous to the "Print" function described above, but functions to clear the selected data from the memory of the pulse oximeter instrument 1. The "Avg" submenu category sets the data averaging interval to a selected one of the preset choices of: 3, 6, 12 seconds. The user activates the select element 15 of the selector knob 18 when the "Avg" submenu category is displayed on the display 14 and then rotates the selector knob 18 to raise or lower the averaging interval that is presently displayed. Once the desired averaging interval is present on the display 14, the user can again activate the select element 15 of the selector knob 18 to set the averaging interval.

Language Selection Example

The language selection submenu category "LANG?", when selected, causes the readout display device 14 to indicate the language that is presently activated on the pulse oximeter instrument. The pulse oximeter instrument 1 also changes the function of the plurality of positions of the selector knob 18 to map to language choices instead of menu categories. As the user rotates the selector knob 18, again in either direction, the readout display device 14 produces an indication of the options that the user can select. Since this is the menu of language choices, the user can sequence through all of the possible languages that the pulse oximeter instrument 1 has been programmed to display, such as: English, Spanish, German, Italian, French. When the language desired by the user has been located and characterized by readout display device 14 indicating in succinct form an identification of the language, such as: "ESPN?" (the menu selection for Spanish), the user can elect this selection by again depressing the select element 15 of the menu selection device 11. The closure of the push-button switch contacts in the language selection menu when the selector knob 18 is rotated to the position corresponding to Spanish causes the input controller to activate the Spanish language presentation subroutine that causes all displays produced by the pulse oximeter instrument 1 to be presented in the Spanish language. Once the user has made a selection of a particular menu entry within an identified menu category, the pulse oximeter instrument 1 returns to the main menu so that the user can sequence through other menu categories or proceed to perform the various monitoring operations of the pulse oximeter instrument 1.

Menu Category - Alarm/Pulse Audible Settings

The final two menu categories are the audible settings for alarm and pulse. The pulse oximeter instrument 1 generates an audible alarm whenever the present oxygen saturation readings exceed one of the threshold settings that were input by the user, as noted above. In addition, the pulse oximeter instrument 1 can produce an audible output, the repetition of which corresponds to the measured pulse of the monitored patient. The volume of each of these audible outputs can be regulated by the user. The audible output level is set by the user activating the select element of the selector knob 18 when the alarm or pulse menu category is displayed on the display 14 and then rotating the selector knob 18 to raise or lower the volume indication that is presently displayed. The volume settings are represented by icons, as shown in FIG. 3, and correspond to the settings: off, low, medium, high. Once the desired icon corresponding to the volume level is present on the display 14, the user can again activate the select element 15 of the selector knob 18 to set the audible output volume.

Menu Selection Device - Rotary Selector Implementation

In electronic equipment, an interface must be provided to enable the user to input data to the equipment. This function is generally implemented by the use of a shaft-mounted knob 18, which shaft 101 is also connected to some form of transducer 28. As the user rotates the knob 18 in either direction, the rotary motion of the shaft 101 causes the transducer element 28 to generate a signal indicative of the shaft's position, direction of rotation and, optionally, speed of rotation. FIG. 2 illustrates an exploded view of the menu selection device 11 used herein. A rotary encoder, as described in detail below, is used as the transducer element 28. The rotary encoder 28 is attached to housing 111 in a conventional manner, with an O-ring 27 being placed around a threaded portion of the housing of rotary encoder 28, which threaded portion projects through a mounting hole in housing 111. Spanner nut 26 secures rotary encoder 28 in place while bearing 24 is press-fit to the wheel hub 23 and the wheel hub 23 is keyed to the end of shaft 101 and also attached to selector knob 18. The transducer elements, detentes, and push-button switch 28S are all integral elements contained within the housing of rotary encoder 28. The top of selector knob 18 includes a "select" area 15 which comprises a substantially triangular shaped region that is separated from the remainder of the top of the selector knob 18 along two sides to form a cantilever element. The select area 15 can therefore be deflected in a downward direction to contact and depress the shaft 101 of the rotary encoder 28. The depression of shaft 101 causes the closure of a membrane switch 28S built into rotary encoder 28 and located at the bottom of shaft 101. The select area 15 is recessed below the remainder of the top surface of the selector knob 18 to minimize the possibility of inadvertent actuation of the membrane switch 28S in rotary encoder 28. The cantilever that makes up the select area 15 is tapered along its length to permit increased deflection with a reduction in the force necessary to depress the select area 15. A label 21 is provided to cover the select area 15 and prevent the entry of contaminants into the select area 15. The label 21 seals the two open sides of the cantilever and is embossed at the narrow end (apex) of the select area 15 to allow depression of the select area 15 without interference. The embossed area of the label as well as the area that covers the open sides of the select area 15 are without adhesive to avoid any interference with movement of the select area 15.

Optical Rotary Encoder

Figure 4:
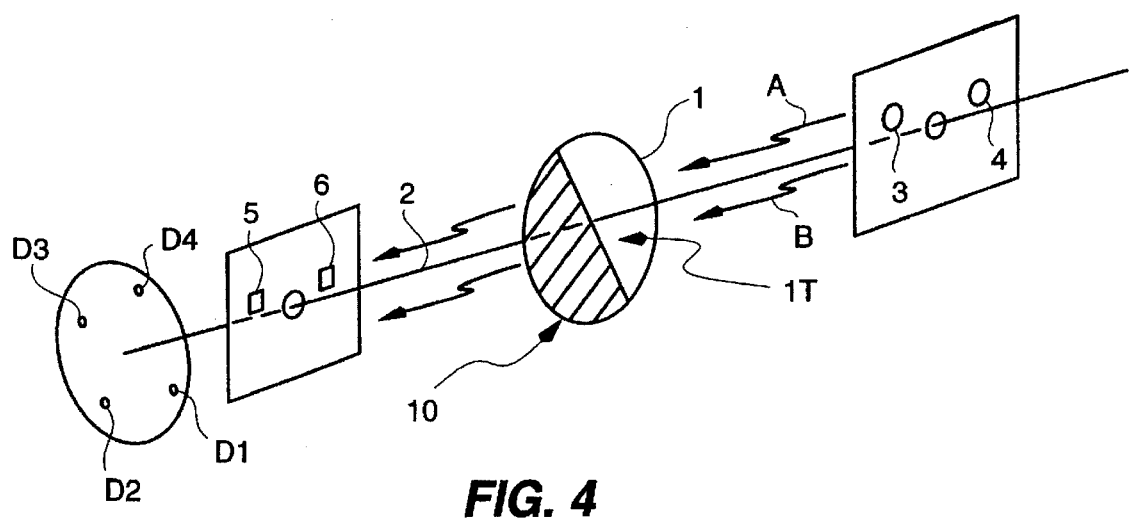
FIG. 4 illustrates the rotary optical encoder apparatus.
Figure 5:
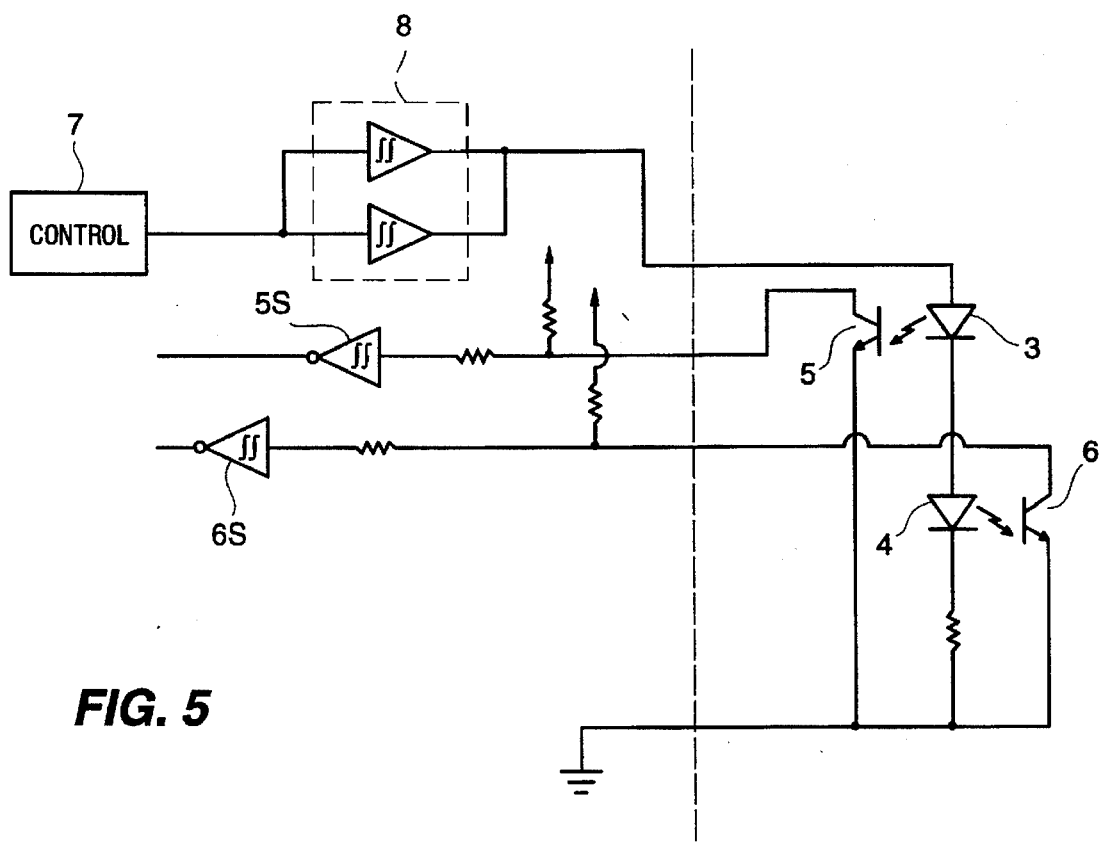
FIG. 5 illustrates the control circuit of the pulsed optical rotary encoder.

The optical rotary encoder 28 makes use of electronic elements to sense the rotary position and motion of the shaft 101. The optical rotary encoder is illustrated in FIG. 4. The basic optical rotary encoder 28 is typically implemented by affixing a chopper disk 1 to a shaft 2, which disk 1 is manufactured of an optically opaque material and which includes at least one light transmissive section 1T formed therein. The optically transmissive sections 1T can be apertures formed in a disk-like structure or the chopper disk 1 can be formed of a plurality of separate optically opaque sections 10 that project radially from a hub affixed to shaft 2. In either case, the resultant structure is termed "disk" herein for simplicity of description. The chopper disk 1 therefore consists of alternating sections of optical transmissivity and optical opacity. A plurality of detentes D1–Dn can be provided to precisely define a plurality of positions of the shaft that correspond to a like plurality of user input selections, with the mechanical feedback provided by the detentes enabling the user to position the shaft in a selected one of the plurality of positions. The number of detentes are selected as a function of the number of alternating opaque/transmitting sections of chopper disk, such that each detented position corresponds to an identifiable pattern of light beam transmission/blocked.

One or more light-emitting devices 3, 4 with corresponding light detectors 5, 6 are installed such that the light beams A and B generated by the light-emitting devices 3, 4 are transmitted to the corresponding light detectors 5, 6 along a path that is parallel to and substantially juxtaposed to the shaft 2. The paths of the two generated light beams A, B are traversed by the chopper disk 1. Thus, the two transmitted light beams A, B are alternately interrupted and passed by the corresponding opaque 10 and transmissive 1T sections of the chopper disk 1 as the chopper disk 1 is rotated via the rotation of shaft 2. As the shaft 2 is rotated and the chopper disk 1 rotates coaxially therewith, the sequence of transmissive 1T and opaque 1O sections of chopper disk 1 cause the light detectors 5, 6 to sense the presence/absence of the light beams A, B transmitted by the light-emitting devices 3, 4. The light detectors 5, 6 produce signals indicative of the presence/absence of one of the opaque sections 1O of the chopper disk 1 being present opposite the corresponding one of light-emitting devices 3, 4. By tracking the sequence of light detector outputs, the control circuit 7 can determine the position of the shaft 2. The use of two light-emitting device/light detector combinations, enables determination of not only the position of the shaft 2, but also the direction of rotation of shaft 2. This is accomplished by placing the light-emitting devices 3, 4 in an offset arrangement such that when the shaft 2 is rotated in a first direction, the apertures formed in the chopper disk 1 pass the light beam A generated by the first light-emitting device 3 immediately prior to passing the light beam B generated by the second light-emitting device 4. When the shaft 2 is rotated in the opposite direction, the chopper disk 1 passes the light beam B generated by the second light-emitting device 4 prior to passing the light beam A generated by the first light emitting device 3. Therefore, the order of light beam transmission is indicative of the direction of rotation of the shaft 2 while the presence or absence of the light beams A, B at the two light detectors 5, 6 is indicative of the position of the shaft 2 and the frequency at which the apertures pass in front of the two light beams A, B is indicative of speed of rotation of the shaft 2.

Therefore, this optical rotary encoder configuration can sense the position of the shaft 2 as well as the direction and speed of rotation thereof without requiring the use of electrical contacts which are a common source of failure in electronic equipment.

Menu Selection Device Control

Figure 7:
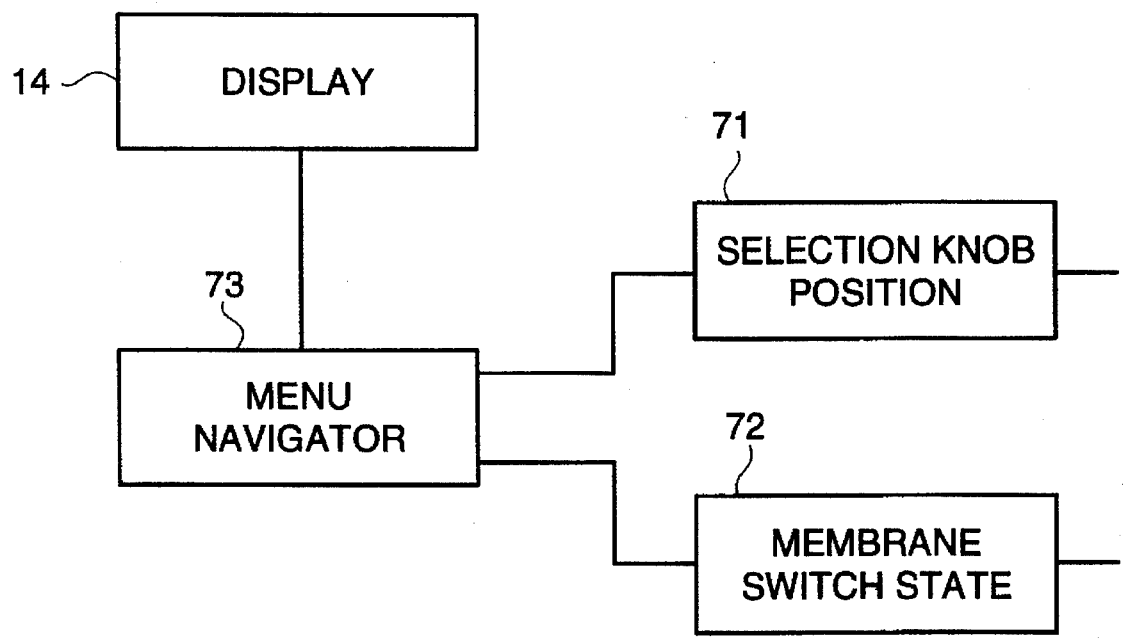
FIG. 7 illustrates in block diagram form the architecture of the menu selection control apparatus.

FIG. 7 illustrates in block diagram form the overall architecture of the control that translates the rotation of selector knob 18 and the operation of select element 15 into a visual display for the user and a corresponding activation of a control function within the pulse oximeter instrument 1. The optical rotary encoder 28 outputs two sets of electrical signals: shaft rotation signals that are indicative of the state of the light detector elements contained in the optical encoder 28, and switch closures indicative of the operation of the membrane switch 28S contained within optical encoder 28 caused by the depression of select element 15 by a user. The set of signals received from optical encoder as well as their temporal sequence determines the menu category (operational characteristic of pulse oximeter 1) and menu item (operational characteristic value of pulse oximeter 1) presently displayed to the user for possible selection.

A selector knob position circuit 71 is connected to the output leads of the rotary encoder 28 that present electrical signals indicative of shaft rotation. The selector knob position circuit 71 identifies the present rotational position of shaft 101 relative to the position of seletor knob 18 at the last power on event. A membrane switch state circuit 72 produces an output signal indicative of the activated state of the membrane switch 28S. Menu navigator circuit 73 translates the temporal sequence of signals received from selector knob position circuit 71 and membrane switch state circuit 72 into a present state of the user's selection in the menu hierarchy that is illustrated in FIG. 3. Thus, menu navigator circuit 73 translates rotation of shaft 101 into a presently displayed menu category when the user is in the top level of the menu. The alphanumeric indication of the presently extant menu category displayed to the user is generated by menu navigator 73 and transmitted to display 14. Activation of the select element 15 results in menu navigator 73 entering the menu category corresponding to the rotational position of selector knob 18 and converting the rotational positions of selector knob 18 into menu entries or submenus as shown in FIG. 3. Subsequent activation of the select element 15 causes menu navigator 73 to activate the menu entry that corresponds to the present rotational position of selector knob 18. The menu navigator 73 transmits control signals to the remaining circuitry in pulse oximeter instrument 1 to indicate both the menu category and menu item that the user has selected. These control signals represent the definition of an operational characteristic or mode of pulse oximeter instrument 1 and a particular user selected value to be assigned to that selected operational characteristic, as described above.

Summary

Thus, the user can perform a significant number of data entry functions that include: setting the date, setting the time. In addition, the user can adjust the operating parameters of the pulse oximeter instrument, such as: set audible alarm volume, adjust alarm threshold level, select language illustrated on display. Furthermore, the user can activate various features and capabilities of the pulse oximeter instrument, such as: print, store readings, erase readings. In order to accommodate this diverse collection of menu selections and data entry items, the menu selection device 11 of the present invention provides a combined menu selection and data entry capability using a single user-activated mechanism. This multi-function capability in a single mechanism is heretofore unknown and enables the user to provide all the required functions using the single menu selection device 11 which is compact enough to fit on the hand-held pulse oximeter instrument 1 and yet large enough to be simple to manipulate by the user.

We claim:

1. A multi-function menu selection apparatus for selecting a one of a plurality of menu entries that are contained in a user selectable hierarchically organized menu, wherein said menu includes a plurality of menu categories, each menu category containing at least one of said plurality of menu entries, comprising:

means, rotatable by a user about an axis to a plurality of predetermined rotational positions, at least two of which rotational positions correspond to ones of said plurality of menu categories, for selecting a one of said plurality of menu categories corresponding to a present rotational position of said selecting means; and means, actuatable in an axial direction along said axis, for enabling said one of said plurality of menu categories selected by said selecting means only in response to actuation of said enabling means in said axial direction.

2. The apparatus of claim 1 wherein said selecting means and said enabling means are both mounted on a single shaft.

3. The apparatus of claim 2 wherein said selecting means comprises a selector knob mounted on an end of said shaft and said enabling means comprises a cantelivered section of said selector knob operable by a user to contact and depress said shaft in said axial direction.

4. The apparatus of claim 1 further comprising:

means for corresponding menu entries of said selected menu category with at least one of said rotational positions of said selecting means.

5. The apparatus of claim 4 further comprising:

means, responsive to said enabling means being activated following selection of a menu category, for activating a menu entry corresponding to a present rotational position of said selecting means.

6. The apparatus of claim 5 wherein at least one of said plurality of menu categories includes at least one submenu as a menu entry, said corresponding means corresponds a submenu with a rotational position of said selecting means when said one menu category is selected by a user.

7. The apparatus of claim 6 wherein said enabling means, in response to said selecting means being rotated to a rotational position corresponding to a submenu and being actuated by a user in an axial direction to select said one said submenu, corresponds submenu entries with at least one of said rotational positions of said selecting means.

8. The apparatus of claim 7 further comprising:

means, responsive to said enabling means being activated following rotation of said selecting means to select a submenu category, for activating a submenu entry corresponding to a present rotational position of said selecting means.

9. The apparatus of claim 5 further comprising:

means for displaying a one of a menu entry, menu category presently selected by a user activating said selecting means and said enabling means.

10. The apparatus of claim 5 wherein said selecting means comprises:

a plurality of mechanical detentes, located in positions to select corresponding predetermined rotational positions of said selecting means.

11. The apparatus of claim 10 wherein said selecting means further comprises:

means for sensing said rotational position of said shaft; and means for converting said sensed rotational position to an electrical signal indicative of said rotational position.

12. The apparatus of claim 11 wherein said corresponding means comprises:

means for translating a presently active combination of said electrical signal and said activation of said enabling means into a corresponding one of menu category, menu entry.

13. The apparatus of claim 12 further comprising:

means for displaying to a user in human readable form said corresponding one of menu category, menu entry presently selected by a user activating said selecting means and said enabling means.

14. A method of selecting a one of a plurality of menu entries that are contained in a user selectable hierarchically organized menu, wherein said menu includes a plurality of menu categories, each menu category containing at least one of said plurality of menu entries, using apparatus attached to a shaft that is rotatable by a user about an axis and also actuatable in an axial direction along said axis, said shaft being rotatable to a plurality of rotatable positions, at least two of which rotatable positions correspond to ones of said plurality of menu categories, comprising the steps of:

selecting a one of said plurality of menu categories corresponding to a present one of said plurality of predetermined rotational positions of said shaft; and enabling said selected one of said plurality of menu categories only in response to axial actuation of said apparatus by a user.

15. The method of claim 14 further comprising the step of:
corresponding menu entries of said selected menu category with at least one of said rotational positions of said shaft.

16. The method of claim 15 further comprising the step of:
activating, in response to said apparatus being axially activated following selection of a menu category, a menu entry corresponding to a present rotational position of said shaft.

17. The method of claim 15 wherein at least one of said plurality of menu categories includes at least one submenu, said step of corresponding corresponds a submenu with a rotational position of said shaft when said one menu category is selected by a user.

18. The method of claim 17 wherein said step of enabling, in response to said shaft being rotated to a rotational position corresponding to a submenu and being actuated by a user in an axial direction to select said one said submenu, corresponds submenu entries with at least one of said rotational positions of said shaft.

19. The method of claim 18 further comprising the step of:
activating, in response to said step of enabling being activated following rotation of said shaft to select a submenu category, a submenu entry corresponding to a present rotational position of said shaft.

20. The method of claim 15 further comprising the step of:
displaying a one of a menu entry, menu category presently selected by a user rotating said shaft and activating said apparatus.

21. A multi-function menu selection apparatus for setting a plurality of operating characteristics of a pulse oximeter instrument, which operating characteristics are contained in a hierarchical menu, wherein said menu includes a plurality of menu categories, each of which corresponds to an operating characteristic of said pulse oximeter, each menu category containing at least one menu entry corresponding to a value of an operating characteristic, comprising:
means, rotatable by a user about an axis to a plurality of predetermined rotational positions, at least two of which rotational positions correspond to ones of said plurality of menu categories, for selecting a one of said plurality of menu categories corresponding to a present rotational position of said selecting means; and
means, actuatable in an axial direction along said axis, for enabling a pulse oximeter operating characteristic corresponding to said one one of said plurality of menu categories selected by said selecting means only in response to actuation of said enabling means in said axial direction.

22. The apparatus of claim 21 wherein said selecting means and said enabling means are both mounted on a single shaft and said selecting means comprises a selector knob mounted on an end of said shaft and said enabling means comprises a cantelivered section of said selector knob operable by a user to contact and depress said shaft in said axial direction.

23. The apparatus of claim 21 further comprising:
means for corresponding pulse oximeter operating characteristic values of said selected pulse oximeter operating characteristic with at least one of said rotational positions of said selecting means.

24. The apparatus of claim 21 further comprising:
means, responsive to said enabling means being activated once an operating characteristic is enabled, for assigning to said enabled operating characteristic, a value that corresponds to a present rotational position of said selecting means.

25. The apparatus of claim 21 wherein at least one of said plurality of menu categories includes at least one submenu, said corresponding means corresponds a submenu with a rotational position of said selecting means when a user selects a menu category that includes said submenu.

26. The apparatus of claim 25 wherein said enabling means, in response to said selecting means being rotated to a rotational position corresponding to a submenu and said enabling means being actuated by a user in an axial direction to select said submenu, corresponds operating characteristic values to at least one of said rotational positions of said selecting means.

27. The apparatus of claim 26 further comprising:
means, responsive to said enabling means being activated following rotation of said selecting means to select an operating characteristic, for activating an operating characteristic value corresponding to a present rotational position of said selecting means.

28. The apparatus of claim 21 further comprising:
means for displaying a one of a operating characteristic, operating characteristic value presently selected by a user activating said selecting means and said enabling means.

29. The apparatus of claim 22 wherein said selecting means comprises a selector knob mounted on an end of said shaft and said enabling means comprises a cantilevered section of said selector knob operable by a user to contact and depress said shaft in said axial direction.

30. A method for setting a plurality of operating characteristics of a pulse oximeter instrument, which operating characteristics are contained in a hierarchical menu, wherein said menu includes a plurality of menu categories, each of which corresponds to an operating characteristic of said pulse oximeter, each menu category containing at least one menu entry corresponding to a value of an operating characteristic, using apparatus attached to a shaft that is rotatable by a user about an axis and also actuatable in an axial direction along said axis said shaft being rotatable to a plurality of rotatable positions, at least two of which rotatable positions correspond to ones of said plurality of menu categories, comprising the steps of:
selecting a one of said plurality of menu categories corresponding to a present one of said plurality of predetermined rotational positions of said shaft; and
enabling a pulse oximeter operating characteristic corresponding to said one menu category selected by said shaft only in response to axial actuation of said apparatus by a user.

31. The method of claim 30 further comprising the step of:
corresponding pulse oximeter operating characteristic values of said selected pulse oximeter operating characteristic with at least one of said rotational positions of said shaft.

32. The method of claim 31 further comprising the step of:
assigning, in response to an operating characteristic being enabled, a value to said enabled operating characteristic that corresponds to a present rotational position of said shaft.

33. The method of claim 30 wherein at least one of said plurality of menu categories includes at least one submenu, said step of corresponding corresponds a submenu with a rotational position of said shaft when a user selects a menu category that includes said submenu.

34. The method of claim 33 wherein said step of enabling, in response to said shaft being rotated to a rotational position corresponding to a submenu and said apparatus being actuated by a user in an axial direction to select said submenu, corresponds operating characteristic values to at least one of said rotational positions of said shaft.

35. The method of claim 34 further comprising the step of:

activating, in response to said apparatus being axially activated following rotation of said shaft to select an operating characteristic, an operating characteristic value corresponding to a present rotational position of said shaft.

36. The method of claim 30 further comprising the step of:

displaying a one of a operating characteristic, operating characteristic value presently selected by a user.

* * * * *